US 6,620,766 B2

United States Patent
Ligon

(10) Patent No.: US 6,620,766 B2
(45) Date of Patent: Sep. 16, 2003

(54) PHYTOPHARMACEUTICAL ALLOY COMPOSITIONS

(75) Inventor: Robert C. Ligon, Raleigh, NC (US)

(73) Assignee: Aventis Cropscience S.A., Lyons (FR)

( * ) Notice: Subject to any disclaimer, the term of this patent is extended or adjusted under 35 U.S.C. 154(b) by 58 days.

(21) Appl. No.: 10/102,150

(22) Filed: Mar. 19, 2002

(65) Prior Publication Data

US 2002/0187901 A1 Dec. 12, 2002

Related U.S. Application Data

(60) Provisional application No. 60/277,325, filed on Mar. 20, 2001.

(51) Int. Cl.[7] .............................................. A01N 37/34
(52) U.S. Cl. ..................... 504/133; 504/141; 504/310
(58) Field of Search ................... 504/133, 141, 504/310

(56) References Cited

U.S. PATENT DOCUMENTS

| | | | |
|---|---|---|---|
| 4,813,999 A | * 3/1989 | Schapira et al. ............. 71/105 |
| 4,936,901 A | 6/1990 | Surgant, Sr. et al. ........... 71/92 |
| 5,160,530 A | 11/1992 | Misselbrook et al. ......... 71/121 |
| 5,374,607 A | 12/1994 | Schapira et al. ............ 504/310 |
| 5,908,632 A | 6/1999 | Nastke et al. ............... 424/417 |

FOREIGN PATENT DOCUMENTS

| | | |
|---|---|---|
| DE | 3702604 A1 | 8/1988 |
| EP | 0 124 993 A1 | 11/1984 |
| EP | 0 404 201 B1 | 7/1997 |
| GB | 1293515 | 10/1972 |
| JP | 43 014819 | of 1968 |
| JP | 48 038855 | 11/1973 |
| JP | 49 013269 | 3/1974 |

OTHER PUBLICATIONS

English Abstract of DE 3702604 A1, Derwent No. 7594679.

International Search Report (4 pages).

* cited by examiner

Primary Examiner—S. Mark Clardy
(74) Attorney, Agent, or Firm—Morgan & Finnegan, L.L.P.

(57) ABSTRACT

Compositions for preparation of wettable-powder and powder suspension herbicidal products containing low-melting agrochemical agents, such as bromoxynil esters, are provided. Preferred compositions are co-melts of bromoxynil esters with at least one additional herbicide or pesticide, particularly atrazine. The compositions of the invention have higher melting points than the bromoxynil ester component, and therefore have advantages in that the use of solvents and/or carriers in formulations can be avoided or minimized. The compositions can be processed into dry powders without the problems associated with the softening or melting of pure bromoxynil esters during grinding or milling, and without the need for dilution of the product with substantial amounts of inactive carriers. Compositions containing the alloys do not lose selectivity in the presence of oil adjuvants.

42 Claims, 1 Drawing Sheet

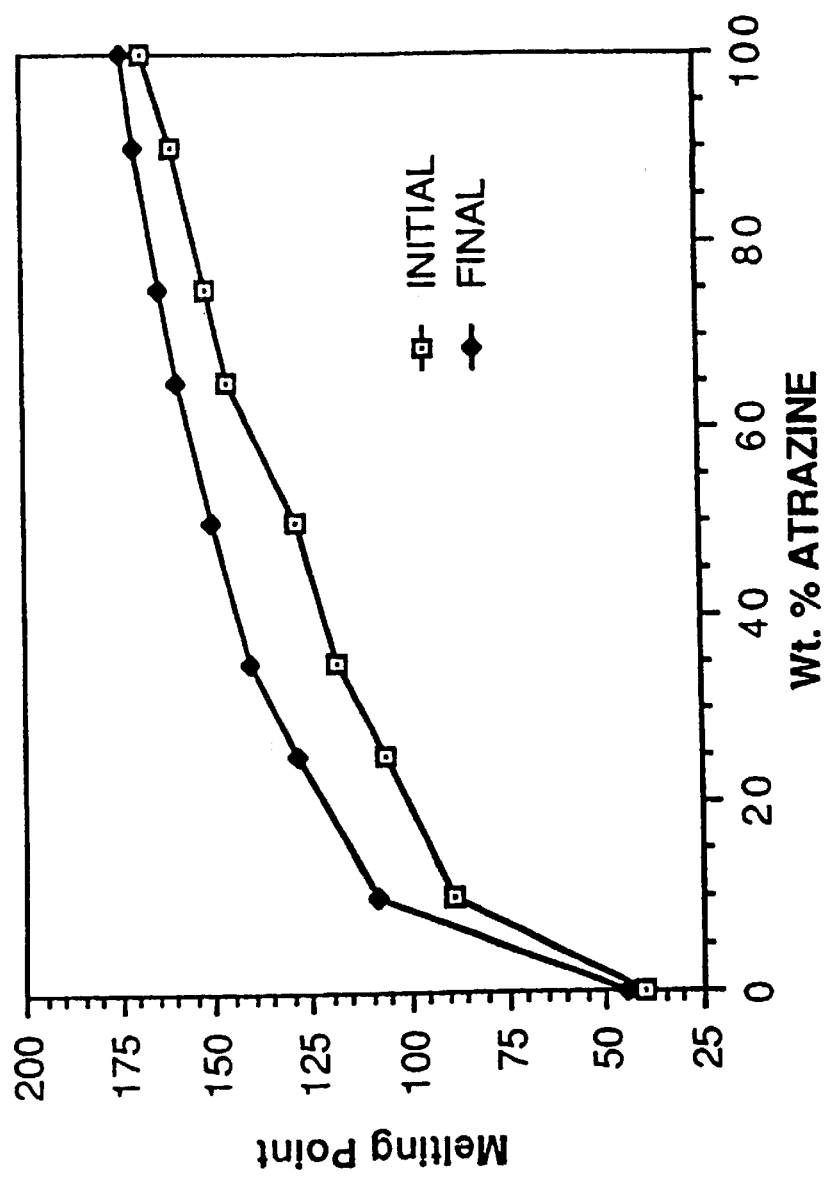

PHYTOPHARMACEUTICAL ALLOY COMPOSITIONS

This application claims benefit of provisional application Ser. No. 60/277,325 filed Mar. 20, 2001.

FIELD OF THE INVENTION

The invention is relevant to the field of herbicides, in particular to dry formulations of herbicides such as wettable powder, water-dispersible granular, and powder suspension herbicidal compositions.

BACKGROUND OF THE INVENTION

Bromoxynil (Ia), a member of the benzonitrile class of photosystem II inhibitors, is a well-known anti-dicot herbicide. It is available in several forms, each of which is associated with certain advantages and disadvantages. Bromoxynil itself, as a free phenol, has good physical properties but is not especially active. The activity of bromoxynil can be improved by formation of ester derivatives. Bromoxynil octanoate (Ib), for example, is more active, but it is less selective; it is also low-melting (m.p. 45–46° C.) and difficult to formulate without fillers or solvents. Bromoxynil butyrate (Ic) is more active than the octanoate, but even less selective, and due to its low melting point it is again necessary to employ organic solvents or fillers in preparing formulations for commercial use. The lower selectivity of the esters leads to a greater degree of damage to crop species, particularly corn, when compared to the free phenols.

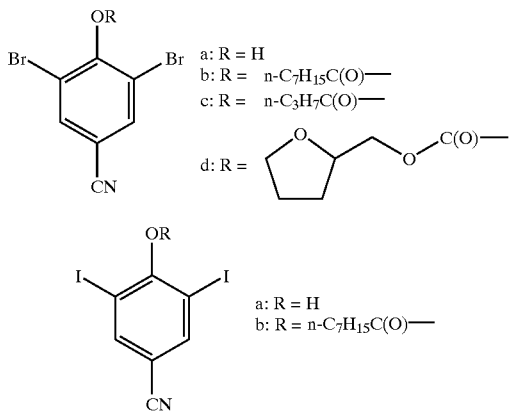

Ioxynil and ioxynil octanoate (IIa and IIb) have similar properties, and similar issues arise with respect to processing and formulating these materials.

Low-melting herbicides may be converted into a solid form by intimate admixture with an inert filler or carrier, such as a clay or silica. For example, U.S. Pat. No. 5,374,607 (incorporated herein by reference) discloses a method of dispersing herbicides on a finely powdered carrier by first dissolving or melting the herbicide ingredient(s), and applying the herbicide(s) in liquid form to the carrier. A similar method of dispersing molten trifluralin on calcium carbonate is described in EP 124,993, and British patent GB 1,293,515 describes melting together propachlor (m.p. 67–76° C.) and atrazine, and dispersing the resulting melt onto attapulgite granules. These methods do avoid the grinding step, and thereby avoid problems with softening or melting of ingredients during grinding, but the presence of a filler leads to compositions having less active ingredient per pound, and requiring correspondingly more resources to package, transport, store, and dispense the final herbicidal product.

Low-melting herbicides may also be microencapsulated by dispersion of the melted substance in an aqueous solution of a film-forming polymer, followed by spray-drying, as described in U.S. Pat. No. 5,160,530 for the low-melting herbicide trifluralin (m.p. 41–43° C.). Microencapsulated alachlor and acetochlor have been combined with atrazine in wettable powder or granular compositions, as described in U.S. Pat. No. 4,936,901, incorporated herein by reference. Spray-drying and microencapsulation, however, entail additional capital expenses for the necessary machinery, and incur energy and other processing costs.

European patent EP 404,201 describes a process of dispersing molten pendimethalin in water, and cooling the resulting suspension, but there is no disclosure that the resulting suspension can be converted into a wettable powder or granular form. German patent DE 3,702,604 describes a similar process in which molten pendimethalin is dispersed into a suspension of atrazine; again there is no disclosure that the resulting suspension can be converted into a wettable powder or granular form.

There remains a need, therefore, for solid forms of low-melting phytopharmaceutical agents, such as bromoxynil and ioxynil, which retain the performance advantages of the agents but which do not have the processing and formulation disadvantages associated with a low melting point.

BRIEF DESCRIPTION OF THE INVENTION

The invention provides co-melts, or alloys, of bromoxynil and ioxynil esters and other low-melting or liquid phytopharmaceutical agents, with higher-melting additional active ingredients. The low-melting phytopharmaceutical agent is preferably a bromoxynil ester. The additional active ingredients may be other pesticides, and are preferably other herbicides. The alloys of the invention are sufficiently high-melting that they may be processed and formulated in a conventional manner without difficulty. In particular, dry formulations, such as wettable powder formulations may be readily produced from the alloys by routine methods, for example by dry grinding or jet-milling the alloys of the invention, without excessive use of inert carriers or fillers. The resulting formulations can therefore contain a higher percentage of active ingredient.

An additional advantage of the invention is improved selectivity of herbicidal compositions which are prepared from the alloys of the invention. It has unexpectedly been found that a formulation of an alloy of the invention is more selective in its herbicidal effects than a comparable formulation containing the same components in a non-alloyed form.

Formulations of the invention comprising bromoxynil octanoate and atrazine are particularly useful for prevention of weed growth, either pre- or post-emergence, in crops such as cotton, cereals, corn and other maize crops, rice, sorghum, alfalfa, mint, onions, garlic, and shallots; and for weed control in pasture and turf areas.

BRIEF DESCRIPTION OF THE FIGURES

FIG. 1 presents the softening point and complete melting temperatures of bromoxynil octanoate/atrazine binary alloys, as a function of alloy composition.

DETAILED DESCRIPTION OF THE INVENTION

The term "alloy" is used herein to designate intimate mixtures of a bromoxynil or ioxynil ester, or other low-melting phytopharmaceutical agent, with one or more other pesticide ingredients, prepared by combining the molten components and then solidifying the molten mixture. The alloys of the invention are not necessarily molecular mixtures. Upon solidification of a co-melt the components may for example (1) crystallize into a co-crystalline form, wherein the crystal unit cell contains molecules of two or more alloy components, and/or (2) form physically discrete microcrystals at some scale (a eutectoid), and/or (3) form a solid solution. The alloys of the invention are characterized by having a melting temperature of 100° C. or higher, and not by the detailed physical distribution of the molecular components. The alloys are not limited to two components, but may optionally include additional ingredients (other than fillers and carriers), whether bioactive or not, such as for example typical herbicide composition ingredients such as processing aids, dispersants, stabilizers, preservatives, and the like. Because the object of preparing the alloy is to obtain a composition having a melting temperature above that of the lowest-melting component, it will be appreciated that the alloys are preferably not eutectic mixtures.

The phrase "low-melting phytopharmaceutical agent" refers to bioactive agrochemical agents, such as herbicides, insecticides, fungicides, and other chemical agents which may usefully be applied to plants or soil, which have melting points below about 100° C. The melting point is preferably below about 80° C., and more preferably below about 60° C. Particularly preferred are those which can be advantageously co-applied with atrazine. Examples include, but are not limited to: bromoxynil esters, ioxynil esters, alachlor (m.p. 39–41° C.), chlorpyrifos (m.p. 41–44° C.), lactofen (m.p. 44–45° C.), azinphos-methyl (m.p. 74° C.), diclofop-methyl (m.p. 39–41° C.), trifluralin (m.p. 46–47° C.), fenoxycarb (m.p. 53–54° C.), cypermethrin (m.p. 60–80° C.), metalaxyl (m.p. 71–72° C.), napropamide (m.p. 74–75° C.), quizalofop-p-ethyl (m.p. 76–77° C.), dicofol (m.p. 78–79° C.; technical grade m.p. 50° C.), and MCPA isooctyl ester. The low-melting phytopharmaceutical agent preferably makes up less than 90% by weight of the alloy, more preferably less than 75%, still more preferably less than 60%, and most preferably less than 50% of the alloy by weight.

The phrases "bromoxynil ester" and "ioxynil ester" refer to derivatives of bromoxynil and ioxynil in which the phenol oxygen is esterified, for example with an aliphatic carboxylic acid or an aliphatic carbonate. Examples include but are not limited to bromoxynil butanoate, ioxynil octanoate, and bromoxynil tetrahydrofurfuryl carbonate (bromobonil, Id). Mixtures of esters, for example a mixture of bromoxynil octanoate and bromoxynil heptanoate, are also intended to be encompassed by the phrase "bromoxynil ester."

The phrase "additional active ingredient" refers to a bioactive agrochemical agent having a melting point sufficiently high to produce an alloy with a low-melting phytopharmaceutical agent as described above, wherein the alloy has a melting point above 100° C. The melting point of the additional active ingredient is preferably above 135° C., more preferably above 150° C., and most preferably above 170° C. The phrase is intended to exclude inorganic fillers and fertilizers, and is intended to include organic chemical pesticides, such as insecticides, fungicides, and herbicides, particularly those which can be advantageously co-applied with bromoxynil or ioxynil esters. Examples of additional active ingredients include, but are not limited to, bromoxynil phenol (m.p. 184° C.), ioxynil phenol (m.p. 212° C.), atrazine (m.p. 175° C.), terbuthylazine (m.p. 177° C.), diuron (m.p. 158° C.), imazamox (m.p. 166° C.), diflufenican (m.p. 161° C.), simazine (m.p. 225° C.), and the like.

The phrase "wettable powder" refers to a finely divided or pulverulent material which, when dispersed in water, produces a stable suspension or dispersion. The phrase is intended to include wettable granular compositions, wherein the powdered material is aggregated into granules so as to reduce airborne dust formation, but still yields a stable suspension or dispersion when combined with water.

It is an object of the invention to provide a herbicidal composition which is an alloy of a phytopharmaceutical agent, preferably a benzonitrile herbicide, and one or more additional bioactive ingredients, where the alloy has a melting point above 100° C. The melting point is preferably above 110° C., more preferably above 120° C., and most preferably above 125° C. The low-melting benzonitrile herbicide is preferably an ester of bromoxynil or ioxynil, more preferably an ester of bromoxynil, and most preferably bromoxynil octanoate. The additional bioactive agent is preferably a pesticide, more preferably a herbicide, and most preferably is atrazine.

It is another object of the invention to provide a method of making an alloy of a phytopharmaceutical agent, preferably a benzonitrile herbicide, and one or more additional bioactive ingredients, where the alloy has a melting point above 100° C., preferably above 110° C., more preferably above 120° C., and most preferably above 125° C.

It is another object of the invention to provide herbicide compositions which comprise making an alloy of a phytopharmaceutical agent, preferably a benzonitrile herbicide, and one or more an additional bioactive ingredients, where the alloy has a melting point of 100° C. or above. These compositions are preferably in the form of wettable powders or water dispersible granules, or suspension concentrates thereof.

The alloys of the invention made by contacting a molten low-melting phytopharmaceutical agent, preferably a benzonitrile herbicide, with a molten additional bioactive ingredient; mixing the molten ingredients; and then permitting or causing the resulting molten mixture to cool until it solidifies. The contacting of the molten components may be accomplished by separately melting the components and then combining the molten ingredients, or alternatively by combining the solid components (with or without mixing) and heating the mixture until it is molten. Other methods, such as adding a solid component to a molten component, can readily be envisioned, and all such obvious variations are contemplated to be within the scope of the invention.

The molten mixture is preferably stirred to homogeneity before it is cooled. The cooling may be accomplished by any means known in the art, for example by pouring the melt onto a cold slab, with or without additional cooling, or by spraying the melt into a colder atmosphere or liquid. The rapidity of the cooling may be varied by routine means, if it is desired to control the melting properties of the alloy. In the case of alloys of bromoxynil esters and atrazine, the speed of cooling appears to have little effect. In general, however, more rapid solidification is expected to produce a well-mixed alloy with a higher melting point, whereas slow solidification is more likely to result in formation of crystallites of the individual components and a broader melting range.

Wettable powder formulations derived from the alloys of the invention may in general be prepared by any method known in the art that could be applied to a pure active ingredient having the same melting point as the alloy. Additives known to the art may be included in the formulation, such as dispersants, wetting agents, fillers, stabilizers, buffers, and the like. Cold milling or cryogenic milling may optionally be employed, if needed to obtain suitably fine powders from alloys that soften excessively during room-temperature processing.

Suitable wetting agents include nonionic and anionic surfactants and dispersants; such as polyethylene-fatty acid esters, phosphate esters, ethoxylated alkyl phenols, polyoxyethylene-fatty alcohol ethers, alkylaryl polyglycol ethers, sodium mono- and di-alkyl sulfonates, sodium alkylsulfates, sodium mono- and di-alkylarylsulfonates, sulfonated kraft lignins, hydroxyalkylmethylcelluloses, polyoxyalkylene block copolymers, sodium alpha-olefin sulfonate, alkylnaphthalene sulfonate formaldehyde condensates, alkyl diphenylether sulfonates, alkyl diphenyloxide disulfonates, polycarboxylates, organosilicone block copolymers, derivatives of the N-methyl fatty acid taurides, sulfo-succinates, tristyrylphenols, ethoxylated alkylamines, alkylpolyglucosides, salts of dodecylbenzene sulfonic acid, and the like.

Suitable dispersants include polyionic surfactants and polyelectrolytes. Examples of dispersants preferred for the formulations of this invention include those sold under the following trade names: Morwet™ D-425, Polyfon™ H, Polyfon™ O, Polyfon™ T, Polyfon™ F, Polyfon™ OD, Lignosol™ XD-65, Reax™ 45L, Reax™ 85A, Reax™ 910, Reax™ 88B, and Reax™ 45A.

Examples of surfactants preferred as wetting agents for the dispersible granule formulations of this invention include those sold under the trade names Morwet™ B, Morwet™ EFW, Morwet™ IP, Sellogen™ DFL, Igepon™ AC-78, Igepon™ T-77, Aerosol™ OT-B, and Triton™ XN-45S.

Examples of dispersants preferred for the water dispersible granule formulations of this invention include: Polyfon H, Polyfon O, Reax 88B, Morwet D-425, Reax 45A, Polyfon T, Polyfon F, Lignosol XD-65, Reax 45L, Reax 85A, Reax 910, Polyfon OD, and PC-825.

Examples of suitable solid diluents or carriers are silica, aluminum silicate, talc, calcined magnesia, kieselguhr, and clays such as kaolin and bentonite.

The wettable powders may contain from 20 to 95% of an alloy of the invention, and they may contain from 0 to 5% of a wetting agent, from 3 to 10% of a dispersant agent and if necessary, from 0 to 10% of one or more stabilizers and/or other additives such as penetrating agents, adhesives or anti-caking agents and colorings.

To prepare a water-dispersible granular (WDG) material, the wettable powder may be granulated on a pan granulator or a disk pelletizer. The granulating fluid will typically be water, but could also contain additional solubilized formulation ingredients, such as wetting agents or buffers as described above. Following granulation, the wet WDG exits the granulating disk, whereupon it is collected and dried, preferably in a fluidized-bed dryer. Other drying methods, such as tray drying, vacuum drying, or oven drying may be used as long as the maximum allowable product temperature is not exceeded. After drying, the WDG is sieved to a uniform granular size, for example 10/40 mesh. The wettable powder formulation also lends itself to other agglomeration techniques, such as for example extrusion, Schugi processing, spray drying, spray agglomeration, or dry compaction.

Aqueous suspension concentrates, which are intended for spray application, are prepared so as to obtain a stable fluid product which does not settle out on standing. They may contain, inter alia, from 20 to 80% of an alloy of the invention, from 0.5 to 15% of surfactants, from 0.1 to 10% of thixotropic agents, and from 0 to 10% of additives such as antifoams, corrosion inhibitors, stabilizers, and buffers; and water as the suspending fluid. Organic substances such as glycols, or inorganic salts, may be added in order to deter sedimentation, or as antifreeze components.

Preferred herbicidal compositions according to the invention are wettable powders and water-dispersible granules.

Where the alloy is an alloy of bromoxynil octanoate and atrazine, the formulations are preferably applied at an overall rate of between 700 and 1300 g/ha of the alloy, more preferably at a rate of between 300 and 500 g/ha of each component. Application of the formulations of the invention is preferably by spraying of an aqueous suspension. The application may be pre- or post-emergence of the weeds whose growth is to be repressed, but is preferably post-emergence.

In applying the compositions of the invention to weeds or soil, it is contemplated that a number of additives and adjuvants may be employed in conjunction with the alloy compositions. Oils, surfactants, and fertilizers, for example, may be combined with or applied with the compositions of the invention.

Postemergence herbicide effectiveness, in particular, is dependent upon spray droplet retention and herbicide absorption by weed foliage. Adjuvants and spray quality therefore influence postemergence herbicide efficacy. Spray additives typically consist of oils, surfactants, and fertilizers. The most effective additive will vary with each herbicide and the need for an additive will vary with environment, weeds present, and herbicide used.

Oils generally are used at 1% v/v (1 gal/100 gal of spray solution) or at 1 to 2 pt/A depending upon herbicide and oil. Oil additives increase herbicide absorption and spray retention. Oil adjuvants are petroleum, vegetable, or methylated vegetable oils plus an emulsifier for dispersion in water spray carriers. The emulsifier, the oil class (petroleum, vegetable, etc.) and the specific type of oil in a class all influence effectiveness of a given oil adjuvant. Methylated seed oils (MSO) generally are equal or better than the other oil classes with all herbicides. Vegetable oils (non-MSO) usually are equal to petroleum oils. The above comparison may differ depending on the specific adjuvant product.

Surfactants are used at 0.12 to 0.5% v/v (1 to 4 pt/100 gal of spray solution). Surfactant levels depend on the amount of active ingredient in the spray and other factors such as weed and crop species and the identity of the herbicides. A major function of a surfactant is to increase the plant spray retention. Surfactants also modulate herbicide absorption. Higher levels of surfactant are used with low levels of herbicide, drought stress, tolerant weeds, or when the surfactant composition contains a low concentration of active ingredient. The effectiveness of a given surfactant will also depend upon the herbicide and its formulation. Information on surfactant effectiveness with a herbicide usually requires field testing, and generally cannot be predicted from surface tension studies.

Fertilizers containing ammonium ions can increase the effectiveness of some herbicides, such as sulfonylurea herbicides. Ammonium ions are involved in herbicide absorption and have enhanced the phytotoxicity of many herbicides. The enhancement of herbicides by nitrogen compounds appears most pronounced with certain species (e.g. velvetleaf and sunflower). Fertilizer applied with certain herbicide formulations may however cause crop injury, as is demonstrated in the examples below.

Those skilled in the art will appreciate that obvious modifications and substitutions can be made in the practice of this invention, and such modifications and substitutions are contemplated to be within the ambit of the invention as set forth more particularly in the claims below.

EXAMPLES

A. Materials

Bromoxynil octanoate, 98%
Urea, 99.5%
Starch, 100%
Ufoxane™, 100% (lignosulfonate dispersant; Borregaard LignoTech, Inc.)
Cellulose acetate, 39.8% acetyl by weight
Atrazine, 97.5%
Reax™ 85a (dispersant;)
Sellogen™ HR (wetting agent)
ASP 400 (clay filler)
Tixosil™ 38 (silica filler)

B. Equipment

Mortar & pestle
Test tubes, 13 mm×100 mm and test tube holder
Oil bath, silicon oil and controller
Petri dishes, 150 mm×20 mm and 60 mm×15 mm
Erlenmeyer Flask, 500 ml
Stainless steel pan, 7.5"×14"
Plastic bag, 12"×14"
Hammer mill, Type MHM-4
Retsch Mill, Type Z-1
Air mill
Malvern Mastersizer™ X

C. Procedure

1. Evaluation of various alloys of bromoxynil octanoate.

Binary mixtures of bromoxynil octanoate (BO) with a variety of additional components were prepared at w:w ratios of 1:2, 1:1, and 2:1. The additional components examined were cellulose acetate, Ufoxane™, starch, urea, and atrazine. Each mixture was ground in a mortar and pestle, then placed in a test tube.

The test tubes were heated in an oil bath at 179° C. to 250° C. to form melts and then poured into petri dishes and allowed to cool. A sample from each petri dish was taken and subjected to a melting point test. Additional samples were assayed by HPLC and NMR to ascertain the quality of the melts.

Additional bromoxynil octanoate and atrazine mixtures were prepared from 40% atrazine to 60% atrazine, in 5% increments. The compositions were melted at 177° C., and once melted, the compositions were poured into large and small petri dishes and stored both at room temperature and at −20° C. for 72 hours. All melts in petri dishes were ground by mortar and pestle and subjected to melting point analysis, a visual check of hardness, and HPLC analysis. NMR analysis was carried out on the 55% atrazine composition.

2. Preparation of wettable powder formulation of BO/atrazine alloy.

Five batches of 50% BO/atrazine alloy were prepared in 500 ml Erlenmeyer flasks. Stainless steel pans were used to collect each batch of 109.6 grams of alloy. The pans were allowed to stand at room temperature for several days to harden. Each pan was scraped and the solids were combined to produce 542 g of alloy. The alloy was passed through a Retsch mill (no screen) to break up the large chips and then 375 g was blended in a plastic bag with 4 inert ingredients: 30 g Reax™ 85a, 15 g Sellogen™ HR, 40 g ASP 400 and 40 g Tixosil™ 38. The blended composition was passed through the Retsch mill using a 3.0-mm screen, to produce 491.2 g of a white powder having black specks.

A small amount of the powder was run through the Retsch mill with a 1.0-mm screen, causing the powder to extrude. The extruded product was set aside and the remainder of the powder was mixed with approximately ⅓ by weight of dry ice. (The dry ice had been reduced to a useable size by running through the Retsch mill without a screen). The particle size of the powder was measured on a Malvern Mastersizer™ X before mixing with dry ice, and found to be 350 $\mu$m D (V, 0.9). After milling with dry ice the powder was found to be 128 $\mu$m D (V, 0.9). This powder was assayed by HPLC and tested for dispersion, solubility and wetting properties, and submitted for a field trial. This powder formulation is referred to below by the internal sample code "TADS 14256A".

3. Field test of wettable powder formulation of BO/atrazine alloy.

The "TADS 14256A" wettable powder formulation was compared to various combinations of herbicidal compositions, by post-emergence spray application of aqueous suspensions to the weed species *Abutilon theophrasti* (velvetleaf) and *Amaranthus rudis* (common waterhemp) in test plots of corn.

All tests were conducted contemporaneously in 10×20 ft (200 ft$^2$) plots, distributed in a single field. Rainfall was recorded daily from planting to the last evaluation date. All treatments were applied as broadcast post-emergent sprays, using a standard small plot sprayer equipped with flat fan nozzles. Crop stage, initial plant heights, and initial leaf counts were determined at the time of application. The targeted weed stages of growth include 4–6 true leaf stage (3–4 inches in height) and 6–8 true leaf stage (5–7 inches in height). Each experiment was conducted in triplicate, i.e. each formulation was applied to three separate and non-adjacent plots.

Percent weed control was determined 13 days after treatment, and percent crop necrosis (chlorosis) was determined at 5 and 13 days after treatment. The results of the trials presented in Table 2 are averages of the triplicate experiments.

D. Results

The results from the first stage of work demonstrated that alloys of BO and atrazine were superior to alloys of BO with other components which were not also small organic molecules. For example, the cellulose acetate co-melt did not completely melt during the melting process at the 1:2 or 2:1 ratios. At a 1:1 ratio the cellulose acetate co-melt became a gum at 226° C., which upon cooling became a glass. The BO/ufoxane co-melt did not completely melt at a 1:2 ratio, and at 1:1 and 2:1 ratios the melt became black at 130–180 ° C. BO/starch at 1:1 melted low, at 44–48° C. The 2:1 ratio melted at 43–45° C. while at the 1:2 ratio melting did not occur until 238–256° C., the decomposition temperature of the starch. The 1:1 bromoxynil/urea mixture melted low, at 44° C., while at 2:1 the urea crystallized first. At a 1:2 ratio the melt was incomplete, and upon visual inspection two immiscible liquids could be observed.

In contrast, bromoxynil octanoate/atrazine alloys, studied from 40 to 60% bromoxynil, proved to form readily and to have very desirable physical properties. Both thick and thin sheets of melts hardened quickly upon cooling. Chemical analysis by HPLC indicated both BO and Atrazine held up to the melting process with no degradation. Using a freezer at −20° C. to accelerate the cool down did not add any benefit in terms of hardening the alloys. The melting points of the compositions indicated that lower proportions of bromoxynil octanoate result in higher melting points. Melting data for a wide range of alloy compositions are presented in Table 1, and graphically in FIG. 1.

TABLE 1

Melting ranges of bromoxynil octanoate/atrazine alloys

| % BO | % atrazine | softening point (° C.) | melting point (° C.) | melting range (° C.) |
|---|---|---|---|---|
| 96.33 | 0 | 40 | 45 | 5 |
| 85.26 | 10.43 | 89 | 109 | 20 |
| 72.77 | 27.14 | 106 | 129 | 23 |
| 59.25 | 32.54 | 119 | 141 | 22 |
| 46.5 | 49.34 | 129 | 150 | 21 |
| 33.82 | 62.51 | 146 | 159 | 13 |
| 26.24 | 77.21 | 152 | 164 | 12 |
| 9.64 | 91.76 | 160 | 170 | 10 |
| 0 | 100.93 | 168 | 174 | 6 |

As can be seen, alloys containing of up to about 50% BO have a high melting point. The melting point of the alloy drops rapidly as the amount of BO rises above 60%. This suggests that alloys containing above 50% BO may require the use of a cryogenic milling process to maintain the integrity of the composition. The sample submitted for NMR analysis indicated no chemical bonding between the two components of the melt.

The field trials demonstrated excellent control (99–100%) of both weed species examined, when the TADS 14256A preparation was employed alone at a rate of 0.93 lbs. active ingredients/acre (LB A/A). Selectivity was also excellent, with no necrosis of the corn crop detected. (See Table 2.)

In Table 2, Buctril™ 2EC is a commercial preparation of bromoxynil octanoate containing the equivalent of two pounds of bromoxynil per gallon, in a petroleum solvent base. Atrazine 90WG is a water-dispersible granule formulation containing 90% atrazine by dry weight. Connect™ 20WP is a commercial wettable powder formulation of bromoxynil octanoate, containing 20% bromoxynil equivalent by weight. Destiny™ L is a methylated soy oil adjuvant, added to improve the spreading of the liquid composition on leaf surfaces. AMS is ammonium sulfate, a nitrogen fertilizer usually co-applied with sulfonylurea herbicides.

It can be seen from Table 2 that the selectivity of the alloy formulations, as measured by corn necrosis (treatment No. 1), is superior to that of a formulation of non-alloyed bromoxynil octanoate and atrazine (treatment No. 3) applied at a comparable rate. This is a surprising result, given that the same active ingredients are present at comparable levels in these two treatments. The presence of an oil adjuvant (Destiny™) does not affect the superior performance (compare treatment No. 5 with treatment No. 6)

Treatment No. 2, which applied Connect™, did not lead to necrosis, whereas necrosis was seen when an equivalent amount of Buctril™ was applied. Buctril™ comprises a liquid organic solvent phase, whereas the solvent in Connect™ is adsorbed onto a carrier. The observation may be related to an effect of the petroleum solvent itself, but it is more likely related to the physical form of the herbicide composition on the surface of the leaf (solid vs. liquid) and the rate of translocation through the leaf surface.

The presence of ammonium sulfate increased the amount of necrosis when Connect™, atrazine, and an oil adjuvant (Destiny™) were applied together (compare treatment No. 6 to treatment No. 9), but did not have an effect when Buctril™, atrazine, and oil adjuvant were applied together (compare treatment No. 7 to treatment No. 10). In all of these treatments necrosis was observed; it appears from the overall results that Buctril™ causes necrosis in corn.

As noted above, the necrosis caused by the Buctril™ formulation of BO is likely to be a result of the petroleum solvent delivering a liquid form of BO directly to the leaf surface, since the wettable powder formulation of BO (Connect™) did not cause necrosis. This is supported by the observation that addition of an oil adjuvant to Connect™ induced corn necrosis (compare treatment No. 2 with treatment No. 6), and that the same oil adjuvant increased the toxicity of Buctril™.

These results are significant, because in terms of coverage of weed species a combination of a bromoxynil herbicide (broad-leaf weeds) and a sulfonylurea (grasses) would be an excellent match. Sulfonylureas are optimally applied with an ammonium fertilizer and with petroleum and oil adjuvants, however, and as shown in Table 2 such additives cause corn necrosis when combined with a bromoxynil ester. The alloy of the present invention retains its selectivity in the presence of such adjuvants (treatment No. 5), and is thus expected to be particularly useful when formulated with sulfonylurea herbicides.

TABLE 2

Repression of weed growth by bromoxynil octanoate and atrazine formulations

| Treatment No. | Name | Form Conc. | Form Type | Rate Rate | Rate Unit | Corn Percent Necrosis 5 DAT | Corn Percent Necrosis 13 DAT | ABUTH PERCENT CONTROL 13 DAT | AMATA PERCENT CONTROL 13 DAT |
|---|---|---|---|---|---|---|---|---|---|
| 1 | TADS 14256A | 73.4 | WP | 0.93 | LB A/A | 0.0 | 0.0 | 99.3 | 100.0 |
| 2 | CONNECT | 20 | WP | 0.38 | LB A/A | 0.0 | 0.0 | 96.0 | 99.3 |
|   | ATRAZINE | 90 | WG | 0.55 | LB A/A |   |   |   |   |
| 3 | BUCTRIL | 2 | C | 0.38 | LB A/A | 10.0 | 5.0 | 100.0 | 100.0 |
|   | ATRAZINE |   |   | 0.55 | LB A/A |   |   |   |   |
| 4 | ATRAZINE | 90 | WG | 0.55 | LB A/A | 0.0 | 0.0 | 86.7 | 97.0 |
| 5 | TADS 14256A | 73.4 | WP | 0.93 | LB A/A | 0.0 | 0.0 | 92.7 | 96.7 |
|   | DESTINY |   | L | 1.5 | PT/A |   |   |   |   |
| 6 | CONNECT | 20 | WP | 0.38 | LB A/A | 6.7 | 1.7 | 100.0 | 100.0 |
|   | ATRAZINE | 90 | WG | 0.55 | LB A/A |   |   |   |   |
|   | DESTINY |   | L | 1.5 | PT/A |   |   |   |   |

TABLE 2-continued

Repression of weed growth by bromoxynil octanoate and atrazine formulations

| Treatment No. | Name | Form Conc. | Form Type | Rate | Rate Unit | Corn Percent Necrosis 5 DAT | Corn Percent Necrosis 13 DAT | ABUTH PERCENT CONTROL 13 DAT | AMATA PERCENT CONTROL 13 DAT |
|---|---|---|---|---|---|---|---|---|---|
| 7 | BUCTRIL | 2 | C | 0.38 | LB A/A | 20.0 | 10.0 | 100.0 | 100.0 |
|   | ATRAZINE | 90 | WG | 0.55 | LB A/A | | | | |
|   | DESTINY | | L | 1.5 | PT/A | | | | |
| 8 | ATRAZINE | 90 | WG | 0.55 | LB A/A | 0.0 | 0.0 | 95.3 | 100.0 |
|   | DESTINY | | L | 1.5 | PT/A | | | | |
| 9 | CONNECT | 20 | WP | 0.38 | LB A/A | 10.0 | 6.7 | 100.0 | 100.0 |
|   | ATRAZINE | 90 | WG | 0.55 | LB A/A | | | | |
|   | DESTINY | | L | 1.5 | PT/A | | | | |
|   | AMS | | WG | 2.0 | LB/A | | | | |
| 10 | BUCTRIL | 2 | C | 0.38 | LB A/A | 20.0 | 10.0 | 100.0 | 100.0 |
|   | ATRAZINE | 90 | WG | 0.55 | LB A/A | | | | |
|   | DESTINY | | L | 1.5 | PT/A | | | | |
|   | AMS | | WG | 2.0 | LB/A | | | | |
| 11 | ATRAZINE | 90 | WG | 0.55 | LB A/A | 0.0 | 0.0 | 98.0 | 100.0 |
|   | DESTINY | | L | 1.5 | PT/A | | | | |
|   | AMS | | WG | 2.0 | LB/A | | | | |

I claim:

1. A composition consisting essentially of an alloy of a low-melting benzonitrile herbicide and one or more additional bioactive ingredients, the alloy having a melting point above 100° C.

2. The composition of claim 1, wherein the alloy has a melting point above 110° C.

3. The composition of claim 1, wherein the alloy has a melting point above 120° C.

4. The composition of claim 1, wherein the alloy has a melting point above 125° C.

5. The composition according to any one of claims 1–4, wherein the low-melting benzonitrile herbicide is an ester of bromoxynil or ioxynil.

6. The composition according to any one of claims 1–4, wherein the low-melting benzonitrile herbicide is an ester of bromoxynil.

7. The composition according to any one of claims 1–4, wherein the low-melting benzonitrile herbicide is selected from the group consisting of bromoxynil butanoate, bromoxynil heptanoate, and bromoxynil octanoate.

8. The composition according to any one of claims 1–4, wherein the low-melting benzonitrile herbicide is a mixture of bromoxynil octanoate and bromoxynil heptanoate.

9. The composition according to any one of claims 1–4, wherein the additional bioactive agent is a pesticide.

10. The composition according to claim 5, wherein the additional bioactive agent is a pesticide.

11. The composition according to claim 6, wherein the additional bioactive agent is a pesticide.

12. The composition according to claim 7, wherein the additional bioactive agent is a pesticide.

13. The composition according to claim 8, wherein the additional bioactive agent is a pesticide.

14. The composition according to any one of claims 1–4, wherein the additional bioactive agent is a herbicide.

15. The composition according to claim 5, wherein the additional bioactive agent is a herbicide.

16. The composition according to claim 6, wherein the additional bioactive agent is a herbicide.

17. The composition according to claim 7, wherein the additional bioactive agent is a herbicide.

18. The composition according to claim 8, wherein the additional bioactive agent is a herbicide.

19. The composition according to any one of claims 1–4, wherein the additional bioactive agent is atrazine.

20. The composition according to claim 5, wherein the additional bioactive agent is atrazine.

21. The composition according to claim 6, wherein the additional bioactive agent is atrazine.

22. The composition according to claim 7, wherein the additional bioactive agent is atrazine.

23. The composition according to claim 8, wherein the additional bioactive agent is atrazine.

24. A method of making a composition consisting essentially of a low-melting phytopharmaceutical agent and one or more additional bioactive ingredients, the low-melting phytopharmaceutical agent having a melting point below 100° C. and the composition having a melting point above 100° C., comprising the steps of:
(a) contacting the molten phytopharmaceutical agent with one or more molten additional bioactive ingredients;
(b) mixing the molten ingredients; and
(c) permitting or causing the resulting molten mixture to cool until it solidifies.

25. The method of claim 24, wherein the low-melting phytopharmaceutical agent is a low-melting benzonitrile ester herbicide.

26. The method according to claim 25, wherein the low-melting benzonitrile herbicide is an ester of bromoxynil or ioxynil.

27. The method according to claim 26, wherein the low-melting benzonitrile herbicide is an ester of bromoxynil.

28. The method according to claim 27, wherein the low-melting benzonitrile herbicide is selected from the group consisting of bromoxynil butanoate, bromoxynil heptanoate, and bromoxynil octanoate.

29. The method according to claim 26, wherein the low-melting benzonitrile herbicide is a mixture of bromoxynil octanoate and bromoxynil heptanoate.

30. The method according to any one of claims 25–29, wherein the additional bioactive agent is a pesticide.

31. The method according to claim 30, wherein the additional bioactive agent is a herbicide.

32. The method according to claim 31, wherein the additional bioactive agent is atrazine.

33. A herbicidal composition comprising an alloy according to any one of claims 1–4, in a formulation chosen from the group consisting of: wettable powder, water-dispersible granules, or suspension concentrate.

34. A herbicidal composition comprising an alloy according to claim 5, in a formulation chosen from the group consisting of: wettable powder, water-dispersible granules, or suspension concentrate.

35. A herbicidal composition comprising an alloy according to claim 6, in a formulation chosen from the group consisting of: wettable powder, water-dispersible granules, or suspension concentrate.

36. A herbicidal composition comprising an alloy according to claim 7, in a formulation chosen from the group consisting of: wettable powder, water-dispersible granules, or suspension concentrate.

37. A herbicidal composition comprising an alloy according to claim 8, in a formulation chosen from the group consisting of: wettable powder, water-dispersible granules, or suspension concentrate.

38. A method of repressing the growth of weeds in soil, comprising applying to the soil an effective amount of a composition according to claim 33.

39. A method of repressing the growth of weeds in soil, comprising applying to the soil an effective amount of a composition according to claim 34.

40. A method of repressing the growth of weeds in soil, comprising applying to the soil an effective amount of a composition according to claim 35.

41. A method of repressing the growth of weeds in soil, comprising applying to the soil an effective amount of a composition according to claim 36.

42. A method of repressing the growth of weeds in soil, comprising applying to the soil an effective amount of a composition according to claim 37.

* * * * *